United States Patent
Hsu

(10) Patent No.: US 10,765,771 B2
(45) Date of Patent: Sep. 8, 2020

(54) AROMATHERAPY LAMP WITH MULTIPLE FUNCTIONS

(71) Applicant: Dong Guan Jia Sheng Lighting Technology Co., Ltd. China, Dong-Guna, Guang-Dong (CN)

(72) Inventor: Kevin Hsu, Taichung (TW)

(73) Assignee: Dong Duan Jia Sheng Lighting Technology Co., Ltd. China, Guang-Dong (CN)

( * ) Notice: Subject to any disclaimer, the term of this patent is extended or adjusted under 35 U.S.C. 154(b) by 77 days.

(21) Appl. No.: 16/232,215

(22) Filed: Dec. 26, 2018

(65) Prior Publication Data

US 2020/0206378 A1 Jul. 2, 2020

(51) Int. Cl.
*A61L 9/03* (2006.01)
*A61L 9/14* (2006.01)
(Continued)

(52) U.S. Cl.
CPC .............. *A61L 9/03* (2013.01); *A61L 9/14* (2013.01); *A61M 21/02* (2013.01);
(Continued)

(58) Field of Classification Search
CPC .......... A61L 9/03; A61L 9/14; A61L 2209/12; A61M 21/02; A61M 2021/0044; A61M 2021/0016
(Continued)

(56) References Cited

U.S. PATENT DOCUMENTS 1,522,755 A * 1/1925 Soreng ............... H05B 3/0033
392/403
3,130,245 A * 4/1964 Banks ................... F24F 6/06
261/29
(Continued)

FOREIGN PATENT DOCUMENTS

CN 203810629 U * 9/2014
CN 205316225 U * 6/2016
(Continued)

OTHER PUBLICATIONS

Machine translation of CN-106322614-A—May, 5, 2020 (Year: 2020).*
(Continued)

*Primary Examiner* — Huy Tram Nguyen
(74) *Attorney, Agent, or Firm* — Alan D. Kamrath; Mayer & Williams PC

(57) ABSTRACT

A lamp includes a lamp body, an acoustics mounted in the lamp body, a light source device mounted in the lamp body, and a humidifying device mounted in the lamp body. The lamp body includes a base, a mounting seat mounted on the base, and a lampshade mounted on the mounting seat. The base has an interior provided with a water storage chamber. The acoustics is mounted in the base. The light source device is mounted on the mounting seat. The humidifying device is mounted on the mounting seat. The humidifying device includes a humidifier mounted on the mounting seat, and a water drawing stick extending through the mounting seat. The water drawing stick has a lower end extending into the water storage chamber, and an upper end connected to the humidifier.

10 Claims, 5 Drawing Sheets

(51) Int. Cl.
*A61M 21/02* (2006.01)
*A61M 21/00* (2006.01)

(52) U.S. Cl.
CPC .. *A61L 2209/12* (2013.01); *A61M 2021/0016* (2013.01); *A61M 2021/0044* (2013.01)

(58) Field of Classification Search
USPC .......................................................... 422/123
See application file for complete search history.

(56) References Cited

U.S. PATENT DOCUMENTS

| | | | | |
|---|---|---|---|---|
| 4,165,835 | A * | 8/1979 | Dearling | A61L 9/12 239/51.5 |
| 6,196,527 | B1 * | 3/2001 | Huang | A61L 9/03 261/142 |
| 6,236,622 | B1 * | 5/2001 | Blackman | G04B 47/00 362/253 |
| 6,877,876 | B1 * | 4/2005 | Steinhilber | F21V 14/025 362/187 |
| 6,902,296 | B2 * | 6/2005 | Searfoss, III | H05B 47/105 362/231 |
| 7,115,155 | B2 * | 10/2006 | Stead | B01D 46/0038 95/218 |
| 8,427,311 | B2 * | 4/2013 | Schlangen | F21V 23/0442 340/540 |
| 2005/0232808 | A1 * | 10/2005 | Smith | A61L 9/03 422/5 |
| 2007/0035044 | A1 * | 2/2007 | Chiu | F24F 6/02 261/81 |
| 2011/0221078 | A1 * | 9/2011 | Lev | A61L 9/03 261/81 |
| 2015/0300581 | A1 * | 10/2015 | Huang | H04R 1/028 362/86 |
| 2017/0319816 | A1 * | 11/2017 | Sokol | G04G 5/00 |

FOREIGN PATENT DOCUMENTS

CN      205807721 U  * 12/2016
CN      106322614 A  *  1/2017

OTHER PUBLICATIONS

Machine translation of CN-203810629-U—May 5, 2020 (Year: 2020).*
Machine translation of CN-205316225-U—May 5, 2020 (Year: 2020).*
Machine translation of CN-205807721-U—May 5, 2020 (Year: 2020).*

* cited by examiner

AROMATHERAPY LAMP WITH MULTIPLE FUNCTIONS

BACKGROUND OF THE INVENTION

1. Field of the Invention

The present invention relates to a lighting tool and, more particularly, to an aromatherapy lamp.

2. Description of the Related Art

A conventional lamp provides an illuminating function. However, the brightness of the conventional lamp cannot be adjusted according to the user's practical requirement, thereby causing an uncomfortable sensation to the user when the light is too strong or too weak. In addition, the conventional lamp only has a single function, and cannot provide an audio function and a humidifying aromatherapy function, thereby greatly decreasing the versatility of the conventional lamp. Further, the user has to additionally provide an audio arrangement or a humidifier to aid the lamp, thereby wasting the space, and thereby increasing the cost.

BRIEF SUMMARY OF THE INVENTION

The primary objective of the present invention is to provide an aromatherapy oil can lamp with multiple functions.

In accordance with the present invention, there is provided a lamp comprising a lamp body, an acoustics mounted in the lamp body, a light source device mounted in the lamp body, and a humidifying device mounted in the lamp body. The lamp body includes a base, a mounting seat mounted on the base, and a lampshade mounted on the mounting seat. The base has an interior provided with a water storage chamber. The base is provided with a water level window aligning with the water storage chamber. The base is further provided with a water entrance connected to the water storage chamber. The mounting seat is provided with a water passage connected to the water storage chamber. The acoustics is mounted in the base. The light source device is mounted on the mounting seat. The humidifying device is mounted on the mounting seat. The humidifying device includes a humidifier mounted on the mounting seat, and a water drawing stick mounted in and extending through the mounting seat. The water drawing stick has a lower end extending into the water storage chamber of the base, and an upper end connected to the humidifier.

According to the primary advantage of the present invention, the lamp integrates the acoustics and the humidifying device, such that the lamp provides multiple functions, thereby enhancing the versatility and diversity of the lamp.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

DETAILED DESCRIPTION OF THE INVENTION

Figure 1:
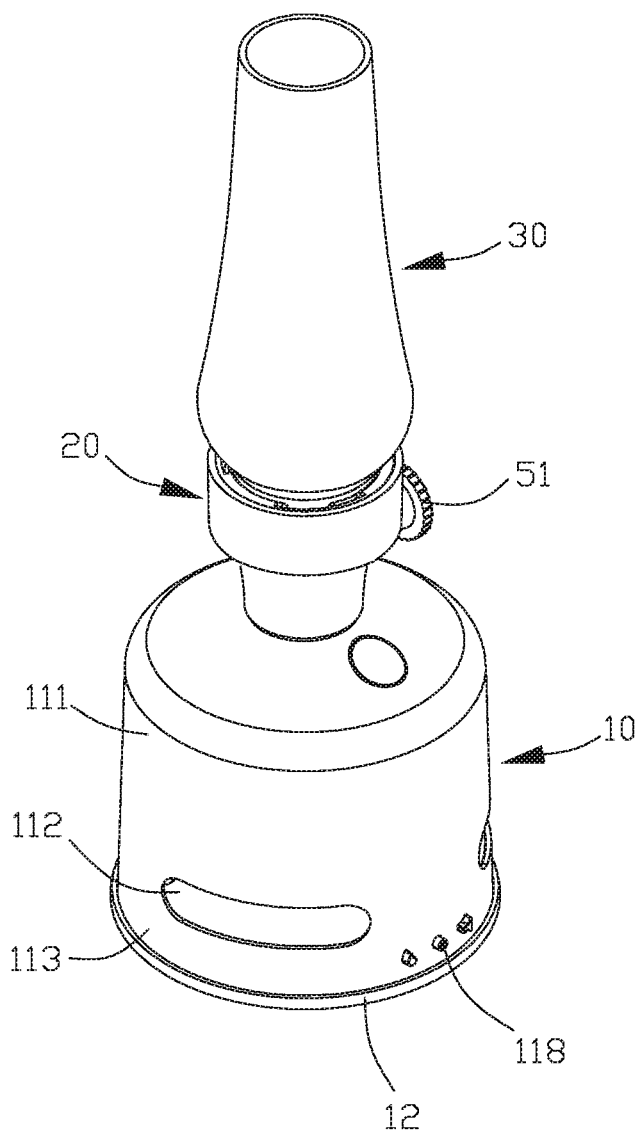
FIG. 1 is a perspective view of a lamp in accordance with the preferred embodiment of the present invention.
Figure 2:
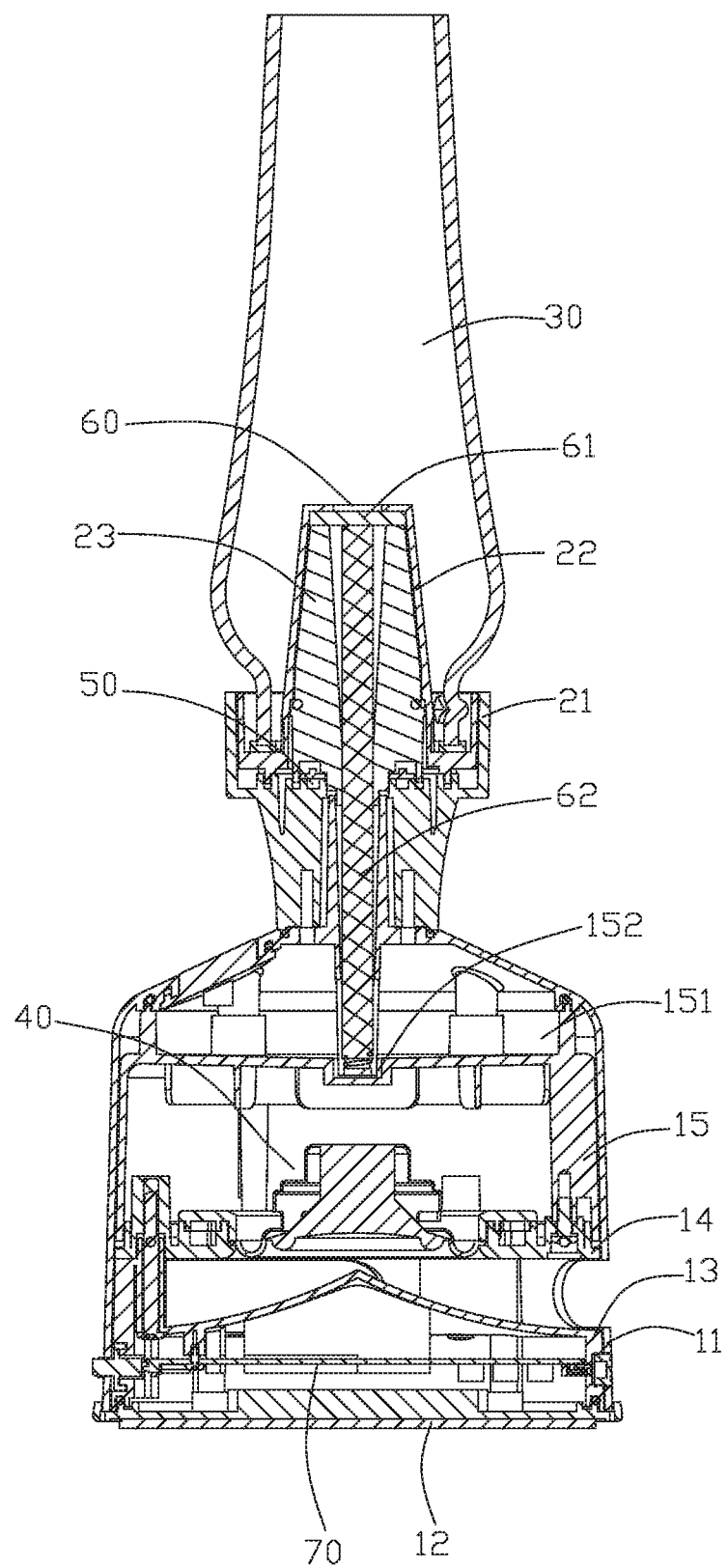
FIG. 2 is a cross-sectional view of the lamp in accordance with the preferred embodiment of the present invention.
Figure 3:
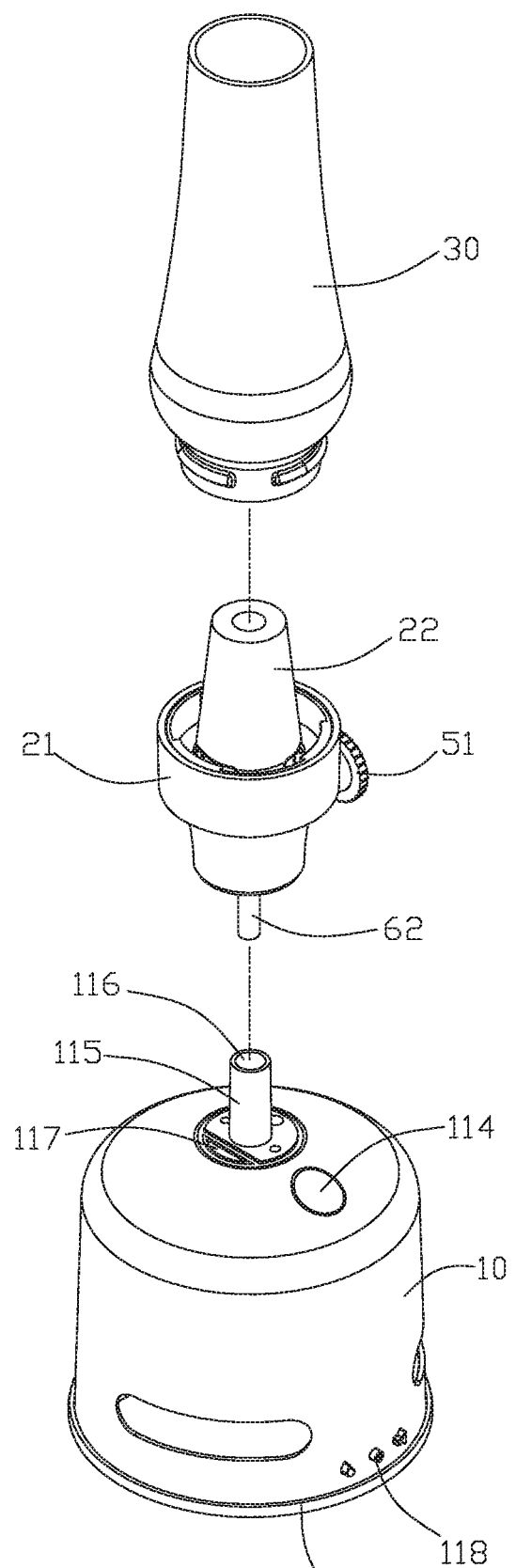
FIG. 3 is a partial exploded perspective view of the lamp in accordance with the preferred embodiment of the present invention.
Figure 4:
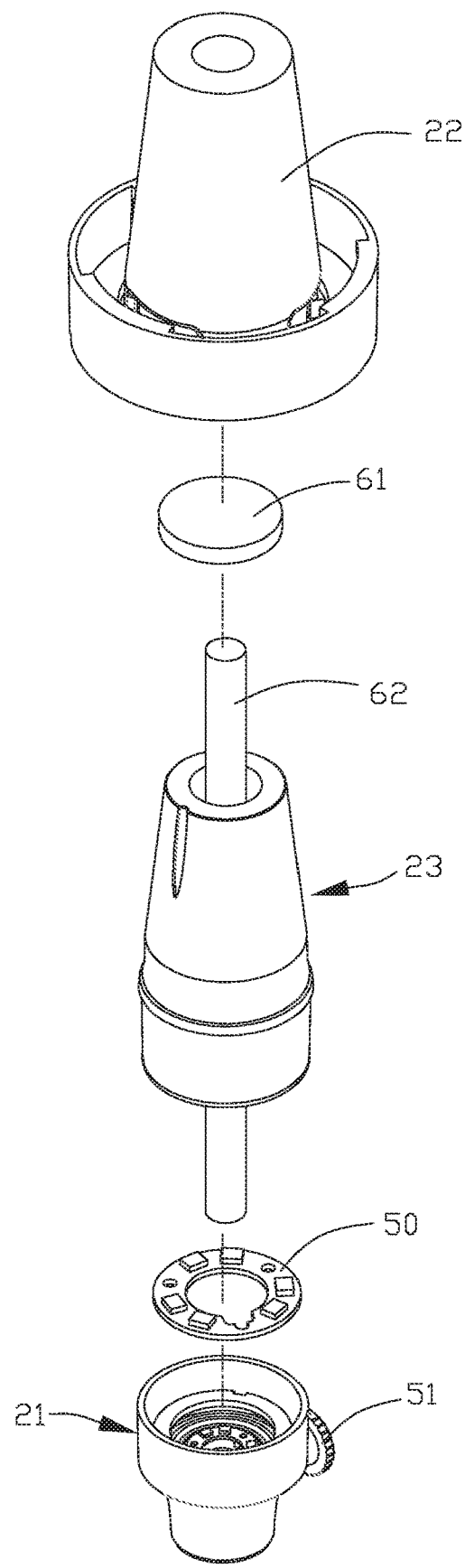
FIG. 4 is another partial exploded perspective view of the lamp in accordance with the preferred embodiment of the present invention.
Figure 5:
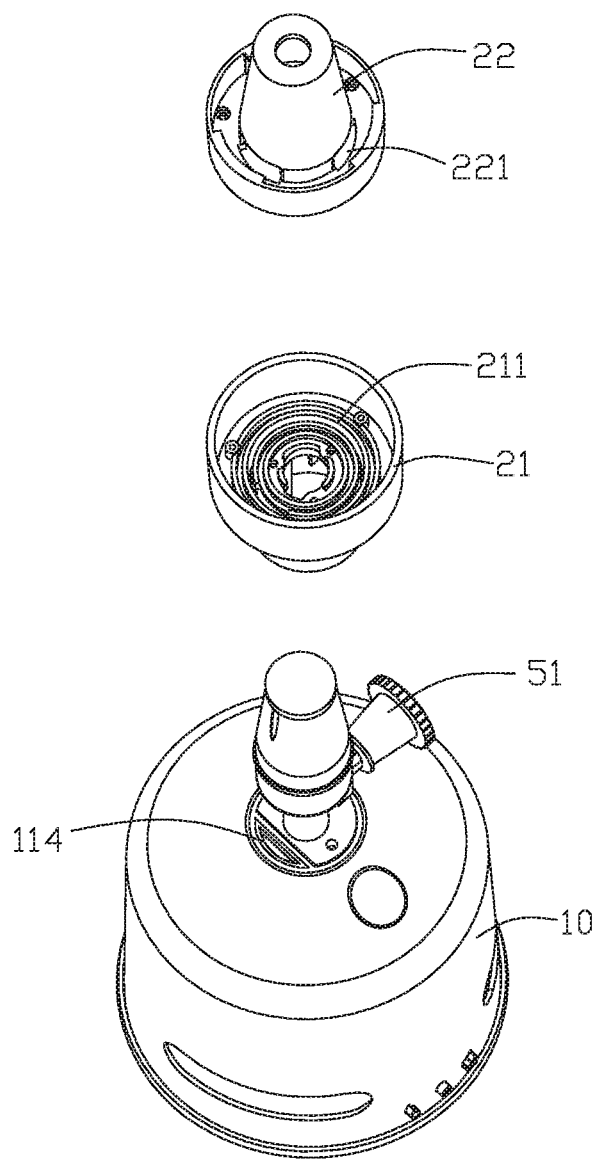
FIG. 5 is another partial exploded perspective view of the lamp in accordance with the preferred embodiment of the present invention.

Referring to the drawings and initially to FIGS. 1-5, a lamp in accordance with the preferred embodiment of the present invention comprises a lamp body, an acoustics (or sound device) 40 mounted in the lamp body, a light source device 50 mounted in the lamp body, and a humidifying device 60 mounted in the lamp body.

The lamp body includes a base 10, a mounting seat 20 mounted on the base 10, and a lampshade 30 mounted on the mounting seat 20. The base 10 has an interior provided with a water storage chamber 151. The base 10 has a surface provided with a water level window 114 aligning with the water storage chamber 151, such that the user observes or inspects the water level of the water storage chamber 151 through the water level window 114. The base 10 is further provided with a water entrance (or water intake or water filling port) connected to the water storage chamber 151.

The mounting seat 20 is provided with a water passage (or water filling channel) connected to the water storage chamber 151. The lampshade 30 is located outside of the mounting seat 20 and partially covers the mounting seat 20. The acoustics 40 is mounted in the base 10. The light source device 50 is mounted on the mounting seat 20.

The humidifying device 60 is mounted on the mounting seat 20. The humidifying device 60 includes a humidifier 61 mounted on the mounting seat 20, and a water drawing (or guiding) stick 62 mounted in and extending through the mounting seat 20. The water drawing stick 62 is disposed at an upright state, and has a lower end extending into the water storage chamber 151 of the base 10, and an upper end connected to the humidifier 61. Preferably, the water drawing stick 62 is a cotton swab. Thus, the lower end of the water drawing stick 62 contacts the water, and the upper end of the water drawing stick 62 is connected to the humidifier 61 to supply the water to the humidifier 61 which atomizes the water (or essence), and the atomized water (or essence) is drained outward from the lampshade 30.

In the preferred embodiment of the present invention, the mounting seat 20 includes an outer pedestal 21, an inner pedestal 22 mounted in the outer pedestal 21, and a hollow fitting pole 23 mounted in a middle of the inner pedestal 22. The humidifier 61 is mounted on a top of the fitting pole 23, and located between the inner pedestal 22 and the fitting pole 23. The water drawing stick 62 is mounted in and extends through the fitting pole 23. Preferably, the light source device 50 is mounted on the bottom of the fitting pole 23 and located between the fitting pole 23 and the outer pedestal 21. The inner pedestal 22 and the fitting pole 23 are preferably made of transparent material.

In the preferred embodiment of the present invention, the base 10 is provided with a water inlet port 117. The inner pedestal 22 is provided with a first water filling hole 221. The outer pedestal 21 is provided with a second water filling hole 211. The water inlet port 117, the first water filling hole 221, and the second water filling hole 211 are connected and form the water passage. Thus, after the lampshade 30 is removed from the mounting seat 20, water (or essence or aroma oil) is directly filled into the first water filling hole 221 of the inner pedestal 22 and is guided into the water storage chamber 151 of the base 10.

In the preferred embodiment of the present invention, the water storage chamber 151 has a middle provided with a restriction groove 152. The base 10 has a top provided with an extension tube 115 which has an interior provided with a through hole 116. The through hole 116 extends through the extension tube 115. The extension tube 115 has an upper end protruding outward from the base 10 and a lower end extending into the restriction groove 152. The water drawing stick 62 is mounted in and extends through the through hole 116 of the extension tube 115.

In the preferred embodiment of the present invention, the lower end of the extension tube 115 has a periphery provided with a connecting hole which is connected to the through hole 116 and the water storage chamber 151.

In the preferred embodiment of the present invention, the connecting hole has a lowermost position lower than a bottom face of the water storage chamber 151, such that the water in the water storage chamber 151 is introduced into the extension tube 115.

In the preferred embodiment of the present invention, the inner pedestal 22 has a top provided with a limit piece which extends toward a middle of the inner pedestal 22 to limit the humidifier 61. The humidifier 61 is located between the limit piece and the water drawing stick 62. A compression spring is biased between the lower end of the water drawing stick 62 and the lower end of the extension tube 115. Thus, the compression spring and the inner pedestal 22 cooperate to position the humidifier 61.

In the preferred embodiment of the present invention, the base 10 includes an outer shell 11, a bottom plate 12 mounted on a bottom of the outer shell 11, and a faceplate 13 covering the bottom plate 12. A receiving space is formed between and defined by the faceplate 13 and the bottom plate 12. The lamp further comprises a power supply 70 mounted in the receiving space of the base 10. The extension tube 115 is mounted on the outer shell 11 of the base 10. The water inlet port 117 is mounted on the outer shell 11 of the base 10. Preferably, the outer shell 11 includes an upper shell part 111 and a lower shell part 113. A plurality of sound emission ports 112 are formed between the upper shell part 111 and the lower shell part 113. The bottom plate 12 covers the bottom of the lower shell part 113. The faceplate 13 is mounted on the lower shell part 113. The water level window 114 is arranged on the upper shell part 111. The outer pedestal 21 of the mounting seat 20 is mounted on the top of the upper shell part 111 and surrounds the extension tube 115. The fitting pole 23 of the mounting seat 20 is mounted on the top of the extension tube 115.

In the preferred embodiment of the present invention, the base 10 further includes an end cap 14 mounted on and located above the faceplate 13, and an inner shell 15 covering the end cap 14. A receiving cavity is formed between and defined by the inner shell 15 and the end cap 14. The acoustics 40 is mounted in the receiving cavity of the base 10. The water storage chamber 151 is provided in a top of the inner shell 15. Preferably, the end cap 14 is arranged in the upper shell part 111. The end cap 14 has a bottom that is gradually recessed upward from the outside toward the inside thereof, and the faceplate 13 has a top that gradually extends upward from the outside toward the inside thereof, such that the bottom of the end cap 14 has a concave (or recessed) structure, and the top of the faceplate 13 has a convex structure, to diffuse or dissipate the audio signals (or sounds) evenly.

In the preferred embodiment of the present invention, the light source device 50 includes a dimmer (or light regulator) 51 mounted on the mounting seat 20. The dimmer 51 is used to regulate the brightness of the light source device 50.

In the preferred embodiment of the present invention, the base 10 is further provided with a plurality of switches 118 that correspond to the acoustics 40, the light source device 50, and the humidifying device 60, so as to turn on/off and regulate the volume of the acoustics 40, to turn on/off the light source device 50, and to turn on/off the humidifying device 60. Preferably, the switches 118 are mounted on the outer shell 11 of the base 10. The base 10 is further provided with an interface that is used for charging or data transmission.

Accordingly, the lamp integrates the acoustics 40 and the humidifying device 60, such that the lamp provides multiple functions, thereby enhancing the versatility and diversity of the lamp. In addition, the lamp saves the space and brings convenience to the user. Further, the brightness of the lamp is regulated freely according to the user's requirement. Further, the acoustics 40 is connected and played by Bluetooth transmission. Further, the humidifying device 60 is added with essence or aroma to provide an aromatherapy.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the scope of the invention.

The invention claimed is:

1. A lamp comprising:
a lamp body;
an acoustics mounted in the lamp body;
a light source device mounted in the lamp body; and
a humidifying device mounted in the lamp body;
wherein:
the lamp body includes a base, a mounting seat mounted on the base, and a lampshade mounted on the mounting seat;
the base has an interior provided with a water storage chamber;
the base is provided with a water level window aligning with the water storage chamber;
the base is further provided with a water entrance connected to the water storage chamber;
the mounting seat is provided with a water passage connected to the water storage chamber;
the acoustics is mounted in the base;
the light source device is mounted on the mounting seat;
the humidifying device is mounted on the mounting seat;
the humidifying device includes a humidifier mounted on the mounting seat, and a water drawing stick mounted in and extending through the mounting seat; and
the water drawing stick has a lower end extending into the water storage chamber of the base, and an upper end connected to the humidifier.

2. The lamp of claim 1, wherein:
the mounting seat includes an outer pedestal, an inner pedestal mounted in the outer pedestal, and a hollow fitting pole mounted in the inner pedestal;
the humidifier is mounted on a top of the fitting pole, and located between the inner pedestal and the fitting pole; and the water drawing stick is mounted in and extends through the fitting pole.

3. The lamp of claim 2, wherein:
the base is provided with a water inlet port;
the inner pedestal is provided with a first water filling hole;
the outer pedestal is provided with a second water filling hole; and
the water inlet port, the first water filling hole, and the second water filling hole are connected and form the water passage.

4. The lamp of claim 2, wherein:
the water storage chamber is provided with a restriction groove;
the base has a top provided with an extension tube which has an interior provided with a through hole;
the extension tube has an upper end protruding outward from the base and a lower end extending into the restriction groove; and
the water drawing stick is mounted in and extends through the through hole of the extension tube.

5. The lamp of claim 4, wherein the lower end of the extension tube has a periphery provided with a connecting hole which is connected to the through hole and the water storage chamber.

6. The lamp of claim 5, wherein the connecting hole has a lowermost position lower than a bottom face of the water storage chamber.

7. The lamp of claim 4, wherein:
the inner pedestal has a top provided with a limit piece which extends toward a middle of the inner pedestal to limit the humidifier;
the humidifier is located between the limit piece and the water drawing stick; and
a compression spring is biased between the lower end of the water drawing stick and the lower end of the extension tube.

8. The lamp of claim 1, wherein:
the base includes an outer shell, a bottom plate mounted on a bottom of the outer shell, and a faceplate covering the bottom plate;
a receiving space is formed between and defined by the faceplate and the bottom plate; and
the lamp further comprises a power supply mounted in the receiving space of the base.

9. The lamp of claim 8, wherein:
the base further includes an end cap mounted on and located above the faceplate, and an inner shell covering the end cap;
a receiving cavity is formed between and defined by the inner shell and the end cap;
the acoustics is mounted in the receiving cavity of the base; and
the water storage chamber is provided in a top of the inner shell.

10. The lamp of claim 8, wherein:
the base is further provided with a plurality of switches that correspond to the acoustics, the light source device, and the humidifying device;
the light source device includes a dimmer mounted on the mounting seat; and
the dimmer regulates brightness of the light source device.

* * * * *